United States Patent
Smith et al.

(10) Patent No.: US 10,149,736 B2
(45) Date of Patent: Dec. 11, 2018

(54) DEPOSITION OF RFID TAGS

(71) Applicants: President and Fellows of Harvard College, Cambridge, MA (US); The Brigham and Women's Hospital, Inc., Boston, MA (US)

(72) Inventors: Michael J. Smith, North Reading, MA (US); Frank L. Hammond, III, Atlanta, GA (US); Robert J. Wood, Cambridge, MA (US); Simon G. Talbot, Boston, MA (US)

(73) Assignees: President and Fellows of Harvard College, Cambridge, MA (US); The Brigham and Women's Hospital, Inc., Cambridge, MA (US)

( * ) Notice: Subject to any disclaimer, the term of this patent is extended or adjusted under 35 U.S.C. 154(b) by 0 days.

(21) Appl. No.: 15/529,035

(22) PCT Filed: Nov. 25, 2015

(86) PCT No.: PCT/US2015/062742
§ 371 (c)(1),
(2) Date: May 23, 2017

(87) PCT Pub. No.: WO2016/086168
PCT Pub. Date: Jun. 2, 2016

(65) Prior Publication Data
US 2017/0258551 A1     Sep. 14, 2017

Related U.S. Application Data

(60) Provisional application No. 62/084,841, filed on Nov. 26, 2014.

(51) Int. Cl.
*A61B 90/98* (2016.01)
*G06K 19/077* (2006.01)
*G16H 40/20* (2018.01)

(52) U.S. Cl.
CPC ........ *A61B 90/98* (2016.02); *G06K 19/07758* (2013.01); *G16H 40/20* (2018.01)

(58) Field of Classification Search
None
See application file for complete search history.

(56) References Cited

U.S. PATENT DOCUMENTS

2006/0170077 A1* 8/2006 Aoki .................. G02F 1/13439
                                                                 257/642
2006/0267202 A1* 11/2006 Matsuzaki .......... H01L 23/5225
                                                                 257/758
2008/0180242 A1* 7/2008 Cottingham ....... G06K 19/0723
                                                                 340/539.12
2009/0309733 A1* 12/2009 Moran ................ G06K 19/041
                                                                 340/572.1

FOREIGN PATENT DOCUMENTS

WO   WO 2013081261 A1 *  6/2013  ............... H01Q 7/00
WO   2015/148901 A1  10/2015

* cited by examiner

*Primary Examiner* — Kristy A Haupt
(74) *Attorney, Agent, or Firm* — Modern Times Legal; Robert J. Sayre

(57) ABSTRACT

In a method for printing an RFID tag on an object, a deposition mask is applied to the surface of an object. With the deposition mask on the surface of the object, RFID materials are deposited on at least one portion of the surface exposed by aperture(s) in the deposition mask. In particular embodiments, RFID tags can be deposited on medical instruments.

13 Claims, 1 Drawing Sheet

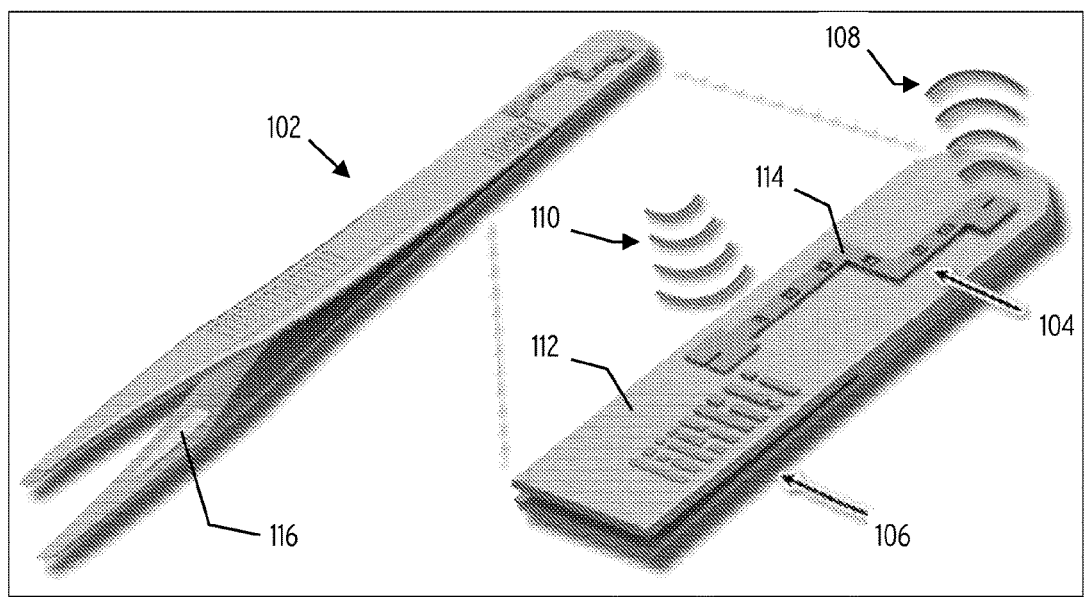

DEPOSITION OF RFID TAGS

BACKGROUND

In hospitals and other facilities, tracking medical instruments and other parts can be challenging and time-intensive. For example, during surgery, a medical instrument (e.g., a clip) may be inadvertently left in the body; and the patient may be stitched up with the instrument left behind. Similarly, an instrument may be recognized as missing after surgery, which raises the question of whether the instrument may have been left in the body. Medical staff may then need to subject the patient to x-ray imaging to look for a missing instrument after surgery; and unnecessary patient exposure to x-rays may be undesirable.

Moreover, may medical instruments may go missing from a medical facility (e.g., a hospital) every day with little ability to track the history of the instrument or even to know what may be missing, and the usage or servicing history of an instrument may not be easily tracked.

BRIEF SUMMARY

A method for depositing a radiofrequency identification (RFID) tag directly on an object is described herein, where various embodiments of the methods may include some or all of the elements, features, and steps described below.

In a method for printing an RFID tag, a deposition mask is applied to a surface of an object. With the deposition mask on the surface of the object, RFID material is deposited on at least one portion of the surface exposed by aperture(s) in the deposition mask.

The manufacturing process for RFID tags described herein can leverage chemical vapor deposition (CVD), physical vapor deposition (PVD), and precise laser machining technologies to print a metallic RFID tag on the surface of an object (e.g., a surgical instrument). This additive manufacturing process uses laser-patterned masks and vapor deposited layers of dielectric material and conductive films deposited by physical vapor deposition (e.g., sputtering or evaporating) to build RFID tags on surfaces of varying composition and curvature. This process has the advantages of (1) inexpensive fabrication, (2) flexibility of RFID tag design, (3) ability to print RFID tags onto pre-existing instruments, eliminating the need for specialized machining, (4) eliminating the need to significantly alter the instrument to accommodate the printed RFID tag (e.g., there is no need to provide a cavity or depression in/on the instrument to accommodate a deposited RFID tag, thereby avoiding any compromise in the structural integrity of the instrument, and (5) enabling printing of the RFID tag onto "out of plane" surfaces.

The RFID tag (or other device, such as a strain gauge) can be deposited directly on an instrument or other object in a single application process with no need to first deposit the tag/gauge on a substrate and to then adhere that substrate to the instrument/object.

The deposition of an RFID tag on a medical instrument allows for detection of missing equipment via RFID scanning when equipment is inadvertently left in a human body after surgery without need for x-rays. For example, the medical instruments in a surgical room can be RFID scanned before and after surgery; and the system can be programmed to detect the absence of any instruments that were scanned before surgery but not after and to trigger an alarm when such an absence is detected. Moreover, as 30,000 or more medical instruments may be used each day in a hospital, tracking those instruments can be extremely labor intensive. The use of deposited RFID tags allows for efficient scanning (and tracking) of each. This allows for logging of its history of use, mechanical sorting during cleaning, locating lost instruments, and ready identification of the instruments via scanning. RFID tags can also be used for instrument selection verification in robotic applications. Knowing the history of an instrument allows a user to readily determine when an instrument has been sent out for service (e.g., sharpening) or to determine how frequently instruments are used to better streamline instrument purchasing or servicing. Computerized mechanical sorting additionally based on instrument identification may additionally streamline the complex task of cleaning and then re-organizing thousands of surgical instruments each day, currently a heavily manual process. Lost instruments taken from the surgical area can be found via RFID stations located throughout the building. Trash receptacles into which medical instruments are discarded can also be RFID scanned (recording signals from RFID tags on instruments that are in the trash) to determine the contents of the trash and thereby enable automated reordering and replacement of those instruments to maintain a consistent stock level. Finally, the details of an instrument, such as what surgical procedure it is used for, the name of it, and even the lifecycle of that particular instrument, can be recorded via scanning.

In addition to their deposition on medical instruments, RFID tags can be deposited on other metal parts or parts made of other materials to facilitate tracking of those parts.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

The FIGURE illustrates an aspect of the subject matter in accordance with one embodiment.

DETAILED DESCRIPTION

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially, though not perfectly pure, as practical and imperfect realities may apply; e.g., the potential presence of at least trace impurities (e.g., at less than 1 or 2%) can be understood as being within the scope of the description; likewise, if a particular shape is referenced, the shape is intended to include imperfect variations from ideal shapes, e.g., due to manufacturing tolerances.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly.

Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

Additionally, the various components identified herein can be provided in an assembled and finished form; or some or all of the components can be packaged together and marketed as a kit with instructions (e.g., in written, video or audio form) for assembly and/or modification by a customer to produce a finished product.

A radio-frequency identification (RFID) system uses tags attached to the objects to be identified. Two-way radio transmitter-receivers (i.e., interrogators or readers) send an electromagnetic signal 110 that is absobed by the RFID tag and read its response.

RFID tags can be passive, active or battery-assisted passive. An active RFID tag has an on-board battery and periodically transmits its ID signal. A battery-assisted passive RFID tag has a small battery on board and is activated when in the presence of an RFID reader. A passive RFID tag has no battery, and its operation is started by illumination with a power level roughly three magnitudes stronger than is needed for signal transmission.

RFID tags typically contain at least the following two parts: (a) an integrated circuit for storing and processing information, modulating and demodulating a radio-frequency (RF) signal, collecting DC power from the incident reader signal, and other specialized functions and (b) an antenna for receiving and transmitting the signal. The tag information is stored in a non-volatile memory. The RFID tag can include either chip-wired logic or a programmed or programmable data processor for processing the transmission and sensor data, respectively. Any of the above-described RFID tags can be used in the apparatus and methods described herein.

An RFID reader transmits an encoded radio signal to interrogate the RFID tag. The RFID tag receives the message and then responds with its identification and other information. The information communicated in the response signal from the RFID tag may be only a unique tag serial number or may be product-related information, such as a stock number, lot or batch number, production date, or other specific information. The RFID tags of this disclosure can be deposited via the same techniques used to deposit strain gauges as described in US Application No. 61/971,727, filed on 28 Mar. 2014, and in the text and drawings that follow. Moreover, the deposition methods described herein can likewise be used to deposit strain gauges in conjunction with the methods described in US Application No. 61/971,727.

In the embodiment illustrated in the FIGURE, a resonator RFID tag 104 and a dipole RFID tag 106 are printed onto an object 102 (in this embodiment, commercially available metallic forceps). In other embodiments, the antennae can be deposited while the ID chip is inserted via a "pick and place" procedure.

The process for printing RFID tags 104/106 involves several steps, including: (1) conditioning of the instrument surface, (2) selective surface masking, (3) deposition of multiple layers of structural and functional materials used to form the RFID components, and (4) a final coating step to protect the RFID tag 104/106. This process can be used to print RFID tags 104/106 on the faces of surgical forceps and the surfaces of cantilever bars and other medical instruments. In various embodiments, the RFID tags 104/106 can be printed along with strain gauges 116 (as described, e.g., in published PCT Application No. WO 2015/148901 A1) and support circuitry.

In the deposition process, the metallic surfaces of the forceps are sanded using high grit sandpaper, sand blasting and/or electropolishing to remove any protective surface coatings and to roughen the surfaces. The forceps are then cleaned with acetone to remove any remaining particles and residue. The surfaces are then coated with several-micron-thick layers of Parylene C (p-xylylene polymer), a moisture resistant, low permittivity polymer that functions as an insulating composition 112. This coating acts as a substrate layer between deposited metal particles and various surface materials and finishes while electrically insulating the metallic surfaces from the RFID tag 104/106. Parylene coating is performed using a PDS 2010 Parylene deposition system (from Specialty Coating Systems, Inc., Indianapolis, Ind., USA) to create even coatings on surfaces of varying curvature and size.

After the surface coating of the insulating composition 112 is applied, deposition masks with micron-sized features are laser-cut from a suitable material [e.g., Kapton polymide tape (DuPont Co., Wilmington, Del., USA)] and tacked onto or positioned upon the surfaces where the RFID tag layer will be deposited. With the deposition masks in place, various constituent metal layers 114 are deposited onto the surfaces using a physical vapor deposition chamber (from Denton Vacuum LLC, Moorestown, N.J., USA).

Deposition masks are replaced and/or superimposed over several physical vapor deposition cycles to create complex 2.5D conductive elements. After deposition of the RFID tags 104, the surfaces of the object 102 (e.g., forceps) are coated again with Parylene (e.g., a 35-μm-thick coating of the p-xylylene polymer) for electrical and chemical insulation and for biocompatibility inside the human body.

Deposition on a Multi-Layer Laminate Structure:

In various embodiments, the RFID tag 104/106, described herein, can be deposited on an object 102 in the form of a pop-up, multi-layer laminated structure, as described in published PCT Application No. WO 2012/109559 A1 and in published PCT Application No. WO 2015/020952 A1. As described in these earlier applications, the layers in the laminate structure can include at least one rigid layer and at least one flexible layer, wherein the rigid layer includes a plurality of rigid segments, and the flexible layer can extend between the rigid segments to serve as a joint. The flexible layers are substantially less rigid than the rigid layers, wherein the rigid layer can have a rigidity that is at least twice as great as or an order of magnitude greater than (e.g., greater than 10× or greater than 100×) the rigidity of the flexible layer; likewise, the flexible layer can have at least 10 times or at least 100 times the flexibility of the rigid layers. The layers can then be stacked and bonded at selected locations to form a laminate structure with inter-layer bonds, and the laminate structure can be distorted or flexed to produce an expanded three-dimensional structure, wherein the layers are joined at the selected bonding locations and separated at other locations.

In one embodiment, the multi-layer laminate structure onto which the RFID tag 104/106 is deposited can be a micro-surgical grasper, as described in published PCT Application No. WO 2015/020952 A1, formed, e.g., of layers of 304 stainless steel, kapton polyimide, and acrylic adhesive.

An RFID tag 104/106 can be deposited/printed (these terms are used interchangeably herein) on an instrument (e.g., a surgical instrument) using the same techniques, described in published PCT Application No. WO 2015/148901 A1, for depositing a strain gauge 116 on an instrument. In contrast, when RFID tags have traditionally been included as a component of an instrument, the RFID tags have been embedded in the instrument, which may produce a significant discontinuity in the structure of the instrument. The deposited RFID tag 104/106 described herein can help to track or identify the instrument on which it is deposited and can interface with, e.g., a robot that probes the tag to determine if is using the appropriate instrument.

Passive RFID tags can be printed on the surfaces of instruments (surgical and non-surgical) for the purpose of identification and traceability. Dipole RF barcodes and spiral resonators do not require rigid components (ICs) for operation and can be interrogated and can respond to ID requests with just the power that the interrogator (scanning device) emits. The FIGURE shows two different RFID tags (i.e., a resonator RFID tag 104 and a dipole RFID tag 106) directly deposited on the surface a pair of forceps. The resonator RFID tag 104 has an adsorption side (for receiving a signal 110) and an emission side (for emitting a signal 108), wherein these sides are differentiated by a difference in conductivity (impedance). The deposited RFID antennae 114 and circuitry can be micro-featured (e.g., with features and dimensions on the scale of 1-100 micrometers).

The instrument surface can be overlaid by the deposition of a base dielectric layer [e.g., comprising Parylene C (poly(p-xylylene))]. The base dielectric layer is then covered with a compliant mask with apertures shaped for forming the desired RFID tag shapes. A metal (e.g., aluminum) with appropriate conductivity and impedance is deposited through these apertures to form the antennae. One or more additional masks can then be applied to the surface with additional deposition through the apertures to form the RFID circuitry in place directly to die-bond pads and sidewalls, thereby eliminating the need for wire bonding.

The mask(s) can be formed of a Kapton polyimide (e.g., 2 mil thick), which conforma well to a curved instrument surface. In other embodiments, the mask(s) can be in the form of a copper film (e.g., 75 micrometers thick) coated with adhesive, which is applied to the instrument surface. The copper/adhesive masks may be more rigid and less subject to curling than the Kapton masks. After deposition of the RFID antennae and circuitry, the deposited RFID tags 104/106 can be encapsulated in a biocompatible coating (e.g., deposited Parylene), wherein the biocompatible coating can also complete the circuit and is tuneable by varying the layer thickness of the coating.

Potential applications for deposition of RFID tags include the following:
  surgical instruments—helping to organize and track instruments, which can prevent injuries caused by instruments left inside a patient after surgery and help improve instrument sorting;
  workshop tools—allowing for tracking of hand tools, drill bits, and other component often lost or misplaced; and
  containers (e.g., for pharmaceuticals)—enabling automated tracking of drug/device inventory.

Experimental:

A few single-bar prototypes of copper resonator RFID tags 104 were deposited on a parylene dielectric layer 112 on metallic surgical instruments 102, and those prototypes were tested. A Denton deposition chamber was used to deposit single bar copper resonator antennae and the RF test the RF response was tested with an HP vector network analyzer in an anechoic chamber. Preliminary results indicate that development of a more-broadband antenna structure may provide a better signal-to-noise difference, allowing for precise measurements for differentiation of the various antenna response frequencies in the band of interest.

Using available RFID tag antennae (built for a lower frequency test previously), we were able to detect the differences between a pair of hemostats outfitted with a printed antenna (single bar resonator) and hemostats with no resonator. The hemostats with no resonator on the surface were barely detected in S11 reflection (in the extreme near field) at −10.84 db at 3.117 GHz. This result constitutes almost no deviation from an empty chamber. Hemostats outfitted with a single-bar resonator were placed into the chamber also in the extreme near field, resulting in an absorption peak of −14.51 db at 3.117 GHz (also in S11 reflection). Transmission power during testing was on the order of 1 mw. Because the hemostats being tested were so close to the antennae (approximately 1 cm away), they are undoubtedly coupling with the detection antenna. Proper testing should be conducted at the far edge of near field (greater than 10 cm) in order to be confident in the results. We can, however, conclude that printed RFID resonators on metallic surgical instruments show promise for detection (in a suitable environment) and characterization in the industrial, scientific and medical (ISM) radio band.

In describing embodiments of the invention, specific terminology is used for the sake of clarity. For the purpose of description, specific terms are intended to at least include technical and functional equivalents that operate in a similar manner to accomplish a similar result. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties or other values are specified herein for embodiments of the invention, those parameters or values can be adjusted up or down by $1/100^{th}$, $1/50^{th}$, $1/20^{th}$, $1/10^{th}$, $1/5^{th}$, $1/3^{rd}$, $1/2$, $2/3^{rd}$, $3/4^{th}$, $4/5^{th}$, $9/10^{th}$, $19/20^{th}$, $49/50^{th}$, $99/100^{th}$, etc. (or up by a factor of 1, 2, 3, 4, 5, 6, 8, 10, 20, 50, 100, etc.), or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention. Further still, other aspects, functions and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety; and appropriate components, steps, and characterizations from these references may or may not be included in embodiments of this invention. Still further, the components and steps identified in the Background section are integral to this disclosure and can be used in conjunction with or substituted for components and steps described elsewhere in the disclosure within the scope of the invention. In method claims, where stages are recited in a particular order—with or without sequenced prefacing characters added for ease of ref.erence—the stages are not to be interpreted as being temporally limited to the order in which they are recited unless otherwise specified or implied by the terms and phrasing.

What is claimed is:

1. A method for depositing a radio frequency identification (RFID) tag on an object, the method comprising:
   depositing an insulating composition on a surface of the object, wherein the insulating composition is at least one of electrically insulating and radiofrequency-electromagnetic-radiation insulating;
   applying a mask on the insulating composition, defining at least one aperture;
   with the mask on the insulating composition, depositing metal through the aperture of the mask to form the RFID tag, wherein the RFID tag has dimensions no greater than about 20 cm;
   depositing a biocompatible material on the deposited metal to form a coating of the biocompatible material on the deposited metal.

2. A method for depositing a radio frequency identification (RFID) tag on an object, the method comprising:
   depositing an insulating composition on a surface of the object, wherein the insulating composition is at least one of electrically insulating and radiofrequency-electromagnetic-radiation insulating;
   applying a mask on the insulating composition, defining at least one aperture; and
   with the mask on the insulating composition, depositing metal through the aperture of the mask to form the RFID tag on a curved surface, wherein the RFID tag has dimensions no greater than about 20 cm.

3. The method of claim 2, further comprising coating the deposited metal with a biocompatible material.

4. The method of claim 3, wherein the biocompatible material comprises a p-xylylene polymer.

5. The method of claim 2, wherein the insulating composition comprises a p-xylylene polymer.

6. The method of claim 2, wherein the insulating composition comprises a carbon black epoxy paste.

7. The method of claim 2, wherein the metal comprises aluminum.

8. The method of claim 7, wherein the metal is deposited by physical vapor deposition.

9. The method of claim 2, wherein the object is a medical instrument.

10. The method of claim 2, wherein the RFID tag is deposited on an out-of-plane surface.

11. The method of claim 2, wherein the RFID tag is deposited on an in-plane surface.

12. An object with a deposited RFID tag, comprising:
    an object with at least one curved surface
    an insulating composition deposited on the surface of the object, wherein the deposited insulating composition is at least one of electrically insulating and radiofrequency-electromagnetic-radiation insulating;
    a metallic RFID tag deposited on a curved surface of the insulating composition, wherein the RFID tag has dimensions no greater than about 20 cm; and
    a biocompatible coating covering the deposited metal RFID tag.

13. The object of claim 12, wherein the object is a medical instrument.

* * * * *